United States Patent [19]

Stephen et al.

[11] Patent Number: 5,222,936
[45] Date of Patent: Jun. 29, 1993

[54] INTRACORPOREAL IONTOPHORETIC METHOD

[76] Inventors: Robert L. Stephen, 2501 Kensington Ave., Salt Lake City, Utah 84108; Franco Lugnani, Viale Miramare 23, 34135 Trieste, Italy; Cino Rossi, Via Settala 32, 00123 Roma, Italy; Silvio Eruzzi, Via A. Mori, 23, 46100 Mantova, Italy

[21] Appl. No.: 765,139

[22] Filed: Sep. 25, 1991

[51] Int. Cl.⁵ .............................................. A61N 1/30
[52] U.S. Cl. ...................................... 604/20; 604/49; 604/21
[58] Field of Search ............... 128/798, 802, 803, 898; 604/20, 21, 49

[56] References Cited

U.S. PATENT DOCUMENTS

| | | | |
|---|---|---|---|
| 4,744,787 | 5/1988 | Phipps et al. | 604/20 |
| 4,747,819 | 5/1988 | Phipps et al. | 604/20 |
| 4,752,285 | 6/1988 | Petelenz et al. | 604/20 |
| 4,915,685 | 4/1990 | Petelenz et al. | 604/20 |
| 5,057,072 | 10/1991 | Phipps | 604/20 |

FOREIGN PATENT DOCUMENTS

| | | | |
|---|---|---|---|
| 825095 | 4/1981 | U.S.S.R. | 604/20 |
| 843999 | 7/1981 | U.S.S.R. | 604/20 |
| 876138 | 10/1981 | U.S.S.R. | 604/20 |
| 1005796 | 3/1983 | U.S.S.R. | 604/20 |
| 1064956 | 1/1984 | U.S.S.R. | 604/20 |

Primary Examiner—Stephen C. Pellegrino
Assistant Examiner—Michael Rafa
Attorney, Agent, or Firm—Jacobson & Johnson

[57] ABSTRACT

A method of intracorporeal iontophoretic treatment of an internal hollow body organ containing a physiological ion-rich fluid environment by delivery to said hollow body organ of drug ions by means of an iontophoretic device inserted into said hollow body organ and comprising an active electrode which has the same polarity as the drug ions to be delivered. The method comprises direct measurement of the pH of said physiological fluid environment, whereby indirectly measuring its ionic composition and selecting accordingly the material of said active electrode so that it either can interact with ions contained in said physiological environment or allow the interaction of said environmental ions with water hydrolysis products so as to reduce the ionic species competitive with said drug ions during the iontophoretic process.

9 Claims, No Drawings

INTRACORPOREAL IONTOPHORETIC METHOD

BACKGROUND OF THE INVENTION

This invention relates to a method of intracorporeal iontophoretic treatment of body cavities or hollow organs. While in the following disclosure specific reference will be made to a preferred embodiment of the invention relating to the treatment of the bladder or prostatic urethra, it is to be understood that the invention is not limited to such treatments but equally applies to the treatment of other body organs meeting the conditions set forth hereinbelow, such as for example vagina.

Iontophoresis is most frequently defined as "the introduction, by means of an electric current, of ions of soluble salts into the tissues of the body for therapeutic purposes" (Dorland's Illustrated Medical Dictionary). The technique of iontophoresis has been in clinical use for more than a century and a great number of drugs have been administered by this method. Some, but by no means all, of the drugs include salts of penicillin, gentamycin, salicylates, fluoride, dexamethasone, hydrocortisone lidocaine, cocaine, morphine and doxorubicin.

By far the most common target site for iontophoretic treatments has been the skin, but the literature also reports a substantial number of treatments directed into the ears, the eyes, the tissues lining the mouth and the teeth. Reports of iontophoretic treatments within bodily cavities, other than the mouth, are very sparse.

In 1983 Davis et al obtained a U.S. Pat. No. 4,411,648, for the purpose of iontophoresing heavy metal ions, such as copper and silver, into the bladder cavity in order to prevent infection. Davis et al described the insertion of both the anode and the cathode into the bladder cavity in order to sterilize volumes of urine within the bladder cavity by means of heavy metal ions derived from the electrode materials themselves.

In chapter 97 of "FOLIA VETENNAVIA" 31, 1 (1987) there is described the treatment of colo-rectal cancers by iontophoresis of the drug, 5-fluorouracil, into the tumor sites using a double balloon catheter. More recently two German patent applications filed in the name of Thiel et al (DE 3809814 and DE 3844518), described iontophoretic delivery of Proflavin and various cogeners into the bladder wall for treatment of bladder cancers. The intravesical volume of drug used was large (200 ml), the currents used were very large (50 m A) and, except for an insulated urethral section and tip, the active electrode within the bladder was an unshielded conductive rod. Although various adjuvants were added to enhance the permeability of the bladder wall, no attempts were made to increase the electrochemical efficiency of drug delivery.

In spite of its inherent attractions iontophoresis has never attained widespread use in therapy probably because of some fundamental electrochemical problems which may be summarized here below.

Theoretically, the quantity (m) of drug (D) delivered by iontophoresis is proportional to the applied current (I) and its time of application:

$$m\, D \approx I.t.$$

Yet it has been shown unequivocally that, with iontophoretic administration of many drugs, the rate of drug delivery progressively diminishes with time. The main reason for this deterioration in performance of the iontophoretic system is associated with the transfer of electrical charge at the electrode (solid) - drug solution interface. For current to flow, electrical charge (electrons) must be transferred across this region. The electrons are derived either from dissolution of the electrode material and/or hydrolysis of water, at the anodic surface. For example:

$$Ag \rightarrow Ag^+ + e^-$$

$$2H_2O \rightarrow 4H^+ + 4e^- + O_2 \uparrow$$

In either case, electrons are provided and unwanted competitive ions ($Ag^+$, $H^+$) are generated.

At the cathode, electrons travel from the electrode into the drug solution, either as negatively charged ions or are again involved in the hydrolysis of water:

$$Ag/AgCl + e^- \longrightarrow Cl^-$$

$$2H_2O + 2e^- \longrightarrow H_2 \uparrow + 2OH^-$$

In order to overcome the disadvantages, and in particular the reduced efficiency of iontophoretic processes due to the accumulation in the iontophoretic environment of the competitive ions originated by the electrodes or by the hydrolysis of water, it has been proposed (e.g. in U.S. Pat. Nos. 4,570,637 and 4,747,819) to coordinate the selection of the electrode material and that of the drug counterion so as to provide during the electrochemical process, ionic species interacting the one with the other so as to minimize or reduce the amount of water hydrolisis products in the iontophoretic process.

None of the prior art references however recognized or dealt with the problems arising in intracorporeal iontophoresis of body cavities where an ion-rich physiological fluid environment exists, and none of them taught how to overcome such problems.

SUMMARY OF THE INVENTION

A main object of the present invention is that of providing a method of intracorporeal iontophoretic treatment of hollow body organs containing an ion-rich physiological environment, which has an improved coulombic efficiency.

Another object of the invention is that of providing an intracorporeal iontophoretic process which requires reduced amounts or concentrations of drug and/or shorter treatment durations than required in the prior art processes.

These and other objects which will appear more clearly from the following disclosure, are achieved by a method of intracorporeal iontophoretic treatment of an internal hollow body organ, containing a physiological ion-rich fluid environment, by delivery to said hollow body organ of drug ions by means of an iontophoretic device insertable in said hollow body organ and comprising an active electrode which has the same polarity as the drug ions to be delivered and is connected to an external electrical circuit which is also connected to a counterelectrode, wherein said method comprises checking the ionic composition of said physiological fluid environment by measuring its pH, selecting accordingly said active electrode from materials allowing ionic species which accumulate in said physiological environment during the iontophoretic process and which are competitive therefore with the drug ions to be diminished by reaction of said competitive ionic species either with the active electrode or with water hydrolysis products, and performing the iontophoretic treatment whereby diminishing said competitive ionic species.

DESCRIPTION OF THE PREFERRED EMBODIMENTS

The present invention is based on the finding that iontophoretic delivery of drugs into an internal body cavity suffers a loss of efficiency because of the electrolyte-rich environment existing therein, which interferes with the desired iontophoretic process.

For instance, effective iontophoretic drug delivery into the bladder wall is always limited by the time of application while effective delivery into the prostatic urethra is potentially limited by time of application, because of continuous, inevitable influx of electrolyte-rich urine into the bladder, and the potential for some of this urine to enter the prostatic urethra during iontophoretic treatments.

Immobilization, or scavenging of at least some of the urinary electrolytes (ions), allows prolongation of effective iontophoretic treatments and increased efficiency of iontophoretic treatments. This desirable result can be achieved by selecting anodal or cathodal materials depending on various incoming urinary electrolytes or by deliberately manipulating certain urinary electrolytes and then selecting an electrode material that will best immobilize these electrolytes by a specific electrochemical reaction.

On the average, urinary volume excreted over 24 hours is about 1500 ml, approximately 1 ml/minute. Urine is usually slightly acid (Ph 5.0–6.5 units), and contains numerous metabolic waste products and also various ionized salts. The total concentration of solutes in urine usually exceeds that in plasma three to five fold.

A list of pertinent urinary ions excreted over 24 hours in this "average" situation is defined in Table 1.

TABLE 1

| URINARY ELECTROLYTES (mEq/24 h.) at pH < 6.5 UNITS | | | |
|---|---|---|---|
| POSITIVE | | NEGATIVE | |
| $Na^+$ | 200 | $Cl^-$ | 200 |
| $K^+$ | 60 | *$HPO_4^{2-} + H_2PO_4^-$ | 40 |
| *$NH^+_4$ | 40 | $SO_4^{2-}$ | 45 |
| $Ca^{2+}$ | 12 | "Acid" salts | 40 |
| $Mg^{2+}$ | 10 | $HCO_3^- + H_2CO_3$ | 1–3 |

*Highly variable

However, there are numerous situations when pH values of urine fall to 4.1–5.0 units (excess H ingestion or production within the body) or rise to 7–8 units (excess alkali ingestion). At times these are caused by illness, frequently they are brought about by some dietary quirk or by a deliberate dietary manipulation. For example, a dilute alkaline urine is of benefit to an individual with a propensity to form uric acid "stones" (gout). In this particular situation, certain urinary ionic contents, especially bicarbonate, chloride and $HPO_4^{2-}/H_2PO_4^-$, differ markedly from levels of the same ions in urine of pH range of 5.0 to 6.5, as shown in Table 2.

TABLE 2

| URINARY ELECTROLYTES (m Eq/24 h.) at pH > 7.0 unit | | | |
|---|---|---|---|
| POSITIVE | | NEGATIVE | |
| $Na^+$ | 200 | $Cl^-$ | 20–30 |
| $K^+$ | 40 | $HPO_4^{2-} + H_2PO_4^-$ | 30–35 |
| $NH_4^+$ | <10 | $SO_4^{2-}$ | 45 |

TABLE 2-continued

| URINARY ELECTROLYTES (m Eq/24 h.) at pH > 7.0 unit | | | |
|---|---|---|---|
| POSITIVE | | NEGATIVE | |
| $Ca^{2+}$ | 10 | "Acid" salts | 40 |
| $Mg^{2+}$ | 8 | $HCO_3^-$ | 150–200 |

Thus, as has been shown above, the pH of urine can range from about 4.1 to about 8.2. Usually the pH variations are determined by reactions of buffering hydrogen ions ($H^+$) produced by metabolic processes. The three major reactions for buffering hydrogen ions are the bicarbonate/carbonic acid, ammonia/ammonium and hydrogen phosphate/dihydrogen phosphate reactions according to the following mechanisms:

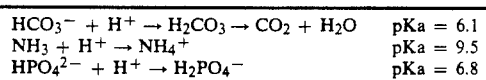

$HCO_3^- + H^+ \rightarrow H_2CO_3 \rightarrow CO_2 + H_2O$   $pKa = 6.1$
$NH_3 + H^+ \rightarrow NH_4^+$   $pKa = 9.5$
$HPO_4^{2-} + H^+ \rightarrow H_2PO_4^-$   $pKa = 6.8$ While the first of the above buffering reactions implies pKa values far outside the physiological pH (about 7.4) of tissues and its only value resides in the body's ability to enzymatically and rapidly convert carbonic acid to $CO_2$, and while the second reaction of above is slow in changing the acid-base balance, the third buffering system is the more versatile in that it has a useful pKa value, it takes place quickly so resulting in rapid modifications of the acid-base balance within the body and has the capacity of immobilizing large quantities of $H^+$, such as at least 100 mM $H^+$daily. Therefore the method of the present invention takes advantage of this body buffer system.

The method of this invention is carried out by means of any iontophoretic device suitable for intracorporeal applications. Illustratively such a device comprises a tubular catheter provided for insertion in a hollow body organ, for example bladder, prostatic urethra or vagina, which contains in its internal tubular cavity an active electrode. The internal cavity of the catheter is a conduit for a solution of a drug in the form of a salt, acid or "alkali", and the catheter is provided on its tubular walls with apertures or holes for the transfer of drug solution to the hollow body organ to be treated.

The polarity of the active electrode used within the catheter depends on the polarity of the drug ion to be delivered. If the drug is in a cationic form, then the active electrode is a positively charged anode, while in the case of a drug in an anionic form the active electrode is a negatively charged cathode. In both cases the active electrode is connected to a generator of current and there is a counterelectrode which closes the electrical circuit and is arranged externally to the body.

According to the present inventive method, the choice of the active electrode material is determined by the ionic content or composition of the physiological fluid environment existing in the body organ to be treated. Such ionic content either can be incidental or spontaneous, or it can be a content intentionally adjusted to a desired range. In either case, according to the present invention, the ionic composition of the physiological fluid environment is assessed through measurement of pH values.

For example, with specific reference to urine environment encountered for example in the bladder or prostatic urethra, Tables 1 and 2 reported herein above show that an acid urine having a pH equal or lower than 6.5 has a high content of chloride ions, while an alkaline urine has a much lesser content of $Cl^-$. Thus it has been found that the simple measurement of urinary pH gives a reasonable estimate of the types and amounts of electrolytes in the urine. For instance two examples of analysis of urinary electrolytes are reported herein below showing the reliability of the relationship taught in the present inventive method between pH and the nature and content of such electrolytes.

| Urine pH = 5.8 units |
| --- |
| $Cl^-$ ~ 200 m Eq/24 h ~ 0.14 mEq/min |
| $HCO_3^-$ and $H_2CO_3$ ~ 2 mEq/24 h |
| $HPO_4^{2-}/H_2PO_4^-$ ~ 1/10 |
| Urine pH = 7.4 units |
| $Cl^-$ ~ 30 mEq/24 h ~ 0.02 mEq/min. |
| $HCO_3^-$ ~ 170 mEq/24 h ~ 0.12 mEq/min. |
| $HPO_4^{2-}/H_2PO_4^-$ ~ 6/1 |

It has been found convenient according to the method of this invention to select the material of the active positive electrode based on the anionic composition of urine which can be estimated from the pH measurement. The material selected is such that it either reacts directly with urine anions or promotes or allows a reaction of such anions with the water hydrolysis ions, so as to achieve an overall reduction of the ionic species accumulating in the iontophoretic environment and competing with the drug ions in the iontophoretic process.

In particular, when the drug to be delivered is in cationic form whereby the active electrode of choice is an anode, the following situations may arise.

(a) The pH of urine is measured as <6.5 units. This pH can be incidental pH, in which case the lower acid values may be due to dietary habits, certain systemic illnesses or to some specific treatment of certain urinary tract infections. Alternatively, this pH values may have been induced deliberately by a preliminary diet, for the purpose of the iontophoretic treatment.

In this situation the anodic material chosen will be a metal giving precipitates by reaction with chloride anions, e.g. silver or copper. The reactions taking place will be:

$Ag \longrightarrow Ag^+; Ag^+ + Cl^- \longrightarrow AgCl$ (insoluble)

$Cu \longrightarrow Cu^+; Cu^+ + Cl^- \longrightarrow CuCl$ (insoluble)

(b) The incidental or intentionally adjusted pH of urine is measured as >7.0. This pH range indicates diminishing quantities of chloride ion (replaced by increasing quantities of bicarbonate ion) and a predominance of hydrogen phosphate ion over dihydrogen phosphate ion. In this case the anode will be selected from substantially inert conductive materials.

With the inert electrode there is hydrolysis of water:

$2H_2O \longrightarrow 4H^+ + O_2 + 4e^-$ then urinary $HPO_4^{2-}$ reacts with hydronium ions:

$HPO_4^{2-} + H^+ \longrightarrow H_2PO_4^-$

Thus, $H^+$ generated by electrolysis of water is scavenged by $HPO_4^{2-}$ in urine whereby $HPO_4^{2-}$ loses charge thus reducing competitive inhibition by urinary ions.

The inert anodes can be selected from carbon, gold, platinum, stainless steel, chromium, nickel-chromium alloys, etc.

c) The measured pH, as an incidental value or as an intentionally adjusted one, is in the range of from 6.5 to 7.0. In this case there still exists an abundant supply of chloride ions in the urine while the $HPO_4^{2-}/H_2PO_4^-$ ratio varies from ½ at pH 6.5 to 1.7/1 at pH 7.0.

Therefore both chloride reactive and inert electrodes can be used, as specified above under points a) and b), respectively, and such electrodes will behave according to the respective reaction mechanisms set forth above to diminish either the chloride ion content or the hydronium ion content and the charge on hydrogen phosphate ion.

When the drug used in the treatment is in anionic form and the active electrode of choice is accordingly a cathode, the options for selecting the cathodic material are more limited. In fact except for few cathodic materials, such as a Ag/AgCl cathode which delivers $Cl^-$ ions, most of the conductive materials used as cathodes cause hydrolysis of water with production of hydroxyl ($OH^-$) ions. According to the principles of the present invention, the useful reaction of hydroxyls with urine ions are those with the dihydrogen phosphate anions and with organic acids present in urine according to the following mechanisms:

$2H_2O + 2e^- \longrightarrow 2OH^- + H_2$ (gas)

$H_2PO_4^- + OH^- \longrightarrow H_2O + HPO_4^{2-}$ $H.Org.Ac. + OH^- \longrightarrow H_2O + Org.Ac.^-$ While these reactions, unlike those taking place at the anode, do not diminish the total charge of the urinary competitive ions, they achieve a neutralization of the hydroxyl ions, which are much more mobile than the relatively bulky drug anions, whereby achieving an overall reduction of unwanted ionic species highly competitive with drug ions for the electrical current.

Since an acid pH of urine shifts the equilibrium of the hydrogen phosphate/dihydrogen phosphate system towards the dihydrogen phosphate thus favouring the above reactions, it is preferred for the purposes of carrying out the method of this invention, to have, when using as active electrode a cathode, an acid urine.

Therefore, if necessary, about 12-24 hours prior to the inventive iontophoretic treatment, the urine pH is brought by a diet, to an acid value, say to a pH of 4.8 to 5.5. Then the cathode material can be selected from any known conductive material behaving as inert cathode, such as gold, carbon, platinum, chromium, nickel-chromium, stainless steel, copper, etc.

By applying the method according to this invention advantages are achieved over prior art iontophoretic methods, especially in terms of reduction of current intensity and/or duration of treatment, thus resulting in a much more effective iontophoretic drug delivery process. In particular, vis-a-vis current intensities of 50 mA and treatment durations of 30' shown in the prior art references, the method of the present invention will achieve a delivery of approximately equal amounts of drugs with currents of 15 to 30 mA for durations of 20 minutes.

Even more importantly, this reduction in the intensity of the electrical current reduces the damage to tissues caused if there is inadvertent direct contact between the active electrodes and the tissues, e.g. the bladder wall.

A drug solution with a concentration of 0.5 to 1.0% by weight is appropriate for clinically effective iontophoretic delivery rates.

The above mentioned improvements achievable by the method of this invention are particularly important not only from a purely economical point of view but also, and more importantly, from the point of view of the patient's comfort and safety.

The following examples are intended as purely illustrative of the various possible embodiments of the present inventive method without limiting in any way the scope of this invention.

EXAMPLE 1

Lidocaine and Mepivacaine (Positively Charged Drug Ion)

In this example, two commonly used local anesthetic agents, lidocaine and mepivacaine have been used.

Twenty eight urological patients having urines with a pH below 6.5 had 100 ml solutions of mepivacaine or lidocaine with epinephrine (a vasoconstrictor) infused into their bladders, prior to endoscopic operative procedures by using a catheter with an active anode of silver. Twenty two of these patients received currents of 10–30 mA for 10–20 minutes with the anode in the bladder and six patients (controls) either had no current applied or had current applied with the cathode in the bladder.

The twenty two experimental subjects tolerated operative procedures with up to 25 grams of bladder tissue removed by cautery. The six control subjects required supplemental intravenous anesthesia or abandonment of the operative procedure.

EXAMPLE 2

Netilmycin Antibiotic (Positively Charged Drug Ion)

A 65 year old male with severe Parkinson's disease had an indwelling bladder catheter for more than 5 years. As almost always occurs, the urine became infected and then the bladder (infective cystitis). Antibiotics were given orally, intramuscularly and directly into the bladder (locally). Susceptible strains of bacteria were eliminated and more resistant strains appeared in their place until, finally, there were present Pseudomonas and Enterobacter bacteria. These two species resisted all attempts at eradication by all appropriate antibiotics administered by all logical routes.

The patient whose urine showed a pH above 7.0 units has received Netilmycin, 900 mg in 100 ml of water, by instillation into the bladder. Iontophoresis using 15 mA over 15 minutes and a gold (inert) electrode was applied. Both Pseudomonas and Enterobacter were eliminated and were replaced by another bacteria, Escherichia Coli. This was an excellent result for the patient because the E. Coli was sensitive to a number of common antibiotics and was eliminated in turn by a course of antibiotics taken by mouth.

We claim:

1. An improved method of intracorporeal iontophoretic administration of ionized drugs to the competitive-ion rich urinary environment of the bladder or prostatic urethra comprising:

feeding into the bladder or prostatic urethra an aqueous solution of a said ionized drug, inserting into the bladder or prostatic urethra an intracorporeal electrode designated to have the same polarity of the drug ions to be administered, electrically connecting said intracorporeal electrode to an external circuit comprising a source of electrical current and a counterelectrode, and applying electrical current from said source, wherein the improvement comprises:

measuring the urine pH prior to said iontophoretic administration whereby assessing the predominant competitive-ions present in the urine, and selecting the material of said intracorporeal electrode in accordance with said pH measurement, the selected electrode material being capable of interacting with said competitive-ions in the urine so as to give products which do not interfere with the iontophoretic drug delivery.

2. A method according to claim 1 further comprising the step of manipulating the predominant urinary competitive-ions to a desired pH range prior to said iontophoretic administration by a preliminary dietary regulation or drug administration.

3. A method according to claim 1 or 2 for administering a cationic drug wherein the measured urinary pH is equal to or less than 6.5 indicating that the predominant urinary competitive-ions comprise chloride ions and wherein the anode to be used as intracorporeal electrode is selected from metals capable of forming chloride precipitates.

4. A method according to claim 3 wherein said anode is selected from the group consisting of silver and copper.

5. A method according to claim 1 or 2 for administering a cationic drug wherein the measured urinary pH is equal to or greater than 7.0 indicating that the predominant urinary competitive-ions comprise bicarbonate ions and monohydrogen phosphate ions and wherein the anode to be used as introcorporeal electrode is selected from essentially inert conductive materials whereby hydrogen ions formed at the anode by water hydrolysis will be available for reacting with said predominant competitive-ions.

6. A method according to claim 5 wherein said anode is selected from the group consisting of carbon, gold, platinum, stainless steel, chromium and nickel-chromium alloys.

7. A method according to claim 1 or 2 for administering a cationic drug wherein the measured urinary pH ranges from 6.5 to 7.0 and wherein the anode to be used as intracorporeal electrode is selected from the group consisting of essentially inert conductive materials and metals forming chloride precipitates.

8. A method according to claim 1 or 2 for administering an anionic drug wherein the measured urinary pH is equal or less than 6.5 indicating that the predominant competitive-ions comprise dihydrogen phosphate and wherein the cathode to be used as intracorporeal electrode is selected from conductive materials behaving as essentially inert cathodes whereby hydroxyl ions produced at the cathode by water hydrolysis will be available to react with said predominant competitive-ions.

9. A method according to claim 8 wherein said cathode is selected from the group consisting of gold, carbon, platinum, stainless steel, copper, chromium and nickel-chromium alloys.

* * * * *